United States Patent
Allen et al.

(10) Patent No.: US 8,513,154 B2
(45) Date of Patent: Aug. 20, 2013

(54) POROUS BODY PRECURSORS, SHAPED POROUS BODIES, PROCESSES FOR MAKING THEM, AND END-USE PRODUCTS BASED UPON THE SAME

(75) Inventors: Timothy L. Allen, Midland, MI (US); Todd R. Bryden, Midland, MI (US); Kevin E. Howard, Midland, MI (US); Steven R. Lakso, Sanford, MI (US); Peter C. Lebaron, Hope, MI (US); Jamie L. Lovelace, Bay City, MI (US); Juliana G. Serafin, Charleston, WV (US); Sten A. Wallin, Midland, MI (US)

(73) Assignee: Dow Technology Investments, LLC, Midland, MI (US)

( * ) Notice: Subject to any disclaimer, the term of this patent is extended or adjusted under 35 U.S.C. 154(b) by 113 days.

(21) Appl. No.: 12/988,316

(22) PCT Filed: Apr. 29, 2009

(86) PCT No.: PCT/US2009/042029
§ 371 (c)(1),
(2), (4) Date: Feb. 25, 2011

(87) PCT Pub. No.: WO2009/134839
PCT Pub. Date: Nov. 5, 2009

(65) Prior Publication Data
US 2011/0136659 A1   Jun. 9, 2011

Related U.S. Application Data

(60) Provisional application No. 61/049,208, filed on Apr. 30, 2008.

(51) Int. Cl.
*B01J 21/00* (2006.01)
*B01J 21/04* (2006.01)
*B01J 23/00* (2006.01)
*B01J 23/02* (2006.01)

(52) U.S. Cl.
USPC ............ 502/232; 502/263; 502/355; 502/439

(58) Field of Classification Search
USPC .................................................. 502/263, 355
See application file for complete search history.

(56) References Cited

U.S. PATENT DOCUMENTS 3,284,369 A * 11/1966 Bergna et al. ................. 502/240
4,112,032 A *  9/1978 Blaszyk et al. ................. 264/42

(Continued)

FOREIGN PATENT DOCUMENTS
JP          8103659 A     4/1996
WO          0187867 A1    11/2001

(Continued)

OTHER PUBLICATIONS

International Search Report and Written Opinion, PCT/US2009/042029, mailed Aug. 21, 2009.

*Primary Examiner* — Patricia L Hailey
(74) *Attorney, Agent, or Firm* — Lois K. Ruzzala; KSJLaw, LLC

(57) ABSTRACT

The present invention provides porous body precursors and shaped porous bodies. Also included are catalysts and other end-use products based upon the shaped porous bodies and thus the porous body precursors. Finally, processes for making these are provided. The porous body precursors, comprise one or more topography-enhancing additives, i.e., additives that are capable of at least marginally enhancing one or more of surface area, aspect ratio, pore volume, median pore diameter, surface morphology, etc. Downstream products need not necessarily comprise the topography-enhancing additives in order to exhibit the benefits of their inclusion in the porous body precursors.

10 Claims, 3 Drawing Sheets

(56) References Cited

U.S. PATENT DOCUMENTS

| | | | |
|---|---|---|---|
| 4,272,443 A | 6/1981 | Titzenthaler et al. | |
| 4,428,863 A | 1/1984 | Fry et al. | |
| 4,575,494 A | 3/1986 | Young et al. | |
| 4,645,754 A | 2/1987 | Tamura et al. | |
| 4,650,622 A * | 3/1987 | Farina | 264/628 |
| 4,769,358 A | 9/1988 | Kishimoto et al. | |
| 4,806,513 A | 2/1989 | McDaniel | |
| 4,965,230 A * | 10/1990 | Nakajima et al. | 501/128 |
| 4,994,588 A * | 2/1991 | Kapicak et al. | 549/534 |
| 5,077,256 A | 12/1991 | Yamamoto et al. | |
| 5,100,859 A | 3/1992 | Gerdes et al. | |
| 5,145,824 A | 9/1992 | Buffum et al. | |
| 5,187,140 A | 2/1993 | Thorsteinson et al. | |
| 5,380,697 A | 1/1995 | Matusz et al. | |
| 5,418,202 A | 5/1995 | Evans et al. | |
| 5,597,773 A | 1/1997 | Evans et al. | |
| 5,703,253 A | 12/1997 | Evans et al. | |
| 5,801,259 A | 9/1998 | Kowaleski | |
| 5,929,259 A | 7/1999 | Lockemeyer | |
| 6,281,370 B1 | 8/2001 | Shima et al. | |
| 6,313,325 B1 | 11/2001 | Shima et al. | |
| 6,407,033 B1 * | 6/2002 | Kimura et al. | 502/350 |
| 6,579,825 B2 | 6/2003 | Lockemeyer | |
| 6,787,656 B2 | 9/2004 | Shima et al. | |
| 6,951,682 B1 * | 10/2005 | Zebala | 428/312.2 |
| 7,026,492 B1 | 4/2006 | Kaminsky | |
| 7,057,056 B1 | 6/2006 | Qin et al. | |
| 7,074,838 B2 | 7/2006 | Colman et al. | |
| 7,102,047 B2 | 9/2006 | Grubbs et al. | |
| 7,211,688 B2 | 5/2007 | Clarke et al. | |
| 7,214,843 B2 | 5/2007 | Beech et al. | |
| 7,238,817 B1 | 7/2007 | Han | |
| 7,256,149 B2 | 8/2007 | Grey et al. | |
| 7,262,334 B2 | 8/2007 | Schmidt et al. | |
| 7,271,117 B2 | 9/2007 | Grey | |
| 7,560,411 B2 | 7/2009 | Yeates et al. | |
| 2003/0191328 A1 | 10/2003 | Jansen et al. | |
| 2007/0111886 A1 | 5/2007 | Serafin et al. | |

FOREIGN PATENT DOCUMENTS

| | | |
|---|---|---|
| WO | 2005023417 A1 | 3/2005 |
| WO | 2006028940 A3 | 3/2006 |

\* cited by examiner

POROUS BODY PRECURSORS, SHAPED POROUS BODIES, PROCESSES FOR MAKING THEM, AND END-USE PRODUCTS BASED UPON THE SAME

FIELD OF THE INVENTION

The present invention provides porous body precursors and shaped porous bodies. Also included are catalysts and other end-use products, such as filters, membrane reactors, composite bodies and the like, based upon the shaped porous bodies and thus the porous body precursors. Finally, processes for making these are provided.

BACKGROUND

Many facets of the practice of chemistry and/or chemical engineering can be reliant upon providing structures or surfaces capable of performing or facilitating separations or reactions and/or providing areas for such separations or reactions to take place. Such structures or surfaces are thus ubiquitous in many R&D and manufacturing settings. Although the desired physical and chemical properties of these shaped bodies can, and will, vary depending on the particular application, there are certain properties that are generally desirable in such shaped bodies regardless of the final application in which they will be utilized.

For example, such shaped bodies will desirably be of high purity and substantially inert so that the shaped bodies themselves will not participate in the separations or reactions taking place around, on or through them in a way that is undesired, unintended, or detrimental. For those shaped bodies for which it is desired to have the components being reacted or separated pass through, or diffuse into, the shaped body, a low diffusion resistance would be advantageous. In certain applications, the shaped bodies are desirably provided within a reaction or separation space, and so they are desirably of sufficient mechanical integrity to avoid being crushed, chipped or cracked during transport or placement. For those shaped bodies desirably utilized as reaction surfaces, high surface area and/or high porosity can be desired, to improve the loading and dispersion of the desired reactants, and also to provide enhanced surface area on which the reactions or separations can take place. Of course, in almost every application, lower cost materials are preferred.

Oftentimes, the desired properties of such shaped bodies can conflict with one another, and as a result, preparing shaped bodies where each desired property is maximized can be challenging. In efforts to meet these challenges, additives or binding agents, have been utilized. However, the use of such agents does not obviate the aforementioned challenge, as the use of such agents can improve one property at the expense of another. Furthermore, additives/binding agents that are desirably added to shaped bodies may require application of additional steps, with their concurrent time and equipment requirements.

Shaped porous bodies having desired properties optimized, or even maximized, would represent a vast improvement to the industry and would be expected to provide substantial benefits to end-use products and applications based thereupon. Processes for producing such shaped porous bodies, desirably without the addition of substantial additional expense in time, materials and/or equipment, would further leverage the benefit provided by such shaped porous bodies.

SUMMARY OF THE INVENTION

The present invention provides such improvements to shaped porous bodies and processes for producing them. Specifically, the present invention provides porous body precursors, upon which shaped porous bodies may be based, comprising at least one topography-enhancing additive. Because the topography-enhancing additive is provided in the porous body precursor, additional steps are not required in order to add it, or the benefits provided thereby, to the shaped porous body, or end-use products based thereupon, and cost and time savings are provided. Further, preferred topography-enhancing additives can be effective without substantially detrimentally impacting other desired properties of the porous body precursors, shaped porous bodies and/or end-use products based thereupon. In fact, in certain especially preferred embodiments, the topography-enhancing additives may advantageously decompose, or otherwise be partially or totally removed during processing of the porous body precursors. The desired topographical improvements may thus be provided, without the shaped porous bodies, or end-use products based thereupon, retaining significant amounts of the topography-enhancing additive. As such, any unintended and/or undesired impact on properties of the shaped porous bodies, as may be provided by other modifiers or additives, may be substantially reduced or even avoided.

In a first aspect, the present invention provides a porous body precursor having incorporated therein at least one topography-enhancing additive. The topography-enhancing additive(s) may be any gas, gaseous or liquid solution, suspension or slurry, or solid composition comprising at least one silicon-containing species, and desirably may be, e.g., colloidal silica, tetraethyl orthosilicate (TEOS), pure silicon, silicon ceramides, silicon containing oils or polymers, $SiF_4$, $SiCl_4$, natural or synthetic silicates (including olivines, sheet-like micas, quartz, feldspars, spinets, pyroxenes, and the like), siloxanes such as tetremethylsiloxane, or combinations of these. Of these colloidal silica, TEOS, natural or synthetic silicates, $SiF_4$, $SiCl_4$ and tetramethylsiloxane, are preferred and pyroxenes and colloidal silica are particularly preferred. Pyroxenes have the general formula $XY(Si,Al)_2O_6$ where X may be calcium, sodium, iron$^{+2}$, magnesium, zinc, manganese or lithium, and Y may be ions of chromium, aluminium, iron$^{+3}$, iron$^{+2}$, magnesium, manganese, scandium, titanium, or vanadium. Particular examples of pyroxenes suitable for use in the present invention include, but are not limited to, clinoenstatite, clinoferrosilite, kanoite, pigeonite, diopside, hedenbergite, johannsenite, petedunnite, augite, omphacite, esseneite, spodumene, jadeite, aegirine, ferrosilite, jervisite, donpeacorite, aegirine-augite, kosmochloror combinations of these. Spodumene ($LiAlSi_2O_6$) is one example of a preferred pyroxene. In addition to the at least one topography-enhancing additive, the porous body precursors desirably comprise transition alumina precursors, transition aluminas, alpha-alumina precursors, or combinations of these.

Because the at least one topography-enhancing additive is added to, and present in, the porous body precursors, additional steps to provide the same, or the benefits provided by the same, to shaped porous bodies based thereupon are not required. A second aspect of the invention thus provides a shaped porous body prepared from a porous body precursor having incorporated therein a topography-enhancing additive. The porous body precursors desirably comprise transition alumina precursors, transition aluminas, alpha-alumina precursors, or combinations of these. As such, the shaped porous bodies may comprise alpha-alumina, and in preferred embodiments may comprise fluoride-affected alpha-alumina. Advantageously, the topography enhancing additives can provide the shaped porous bodies with a greater surface area and can provide the particles of which the shaped porous bodies are comprised with a greater aspect ratio. More particularly, the shaped porous bodies may have surface areas of at least about 0.7 $m^2/g$, or even about 2.0 $m^2/g$, or up to about 3.0 $m^2/g$ and the particles of which the shaped porous bodies are comprised may exhibit aspect ratios of at least 5, or even about 50, or up to about 75.

In a third aspect, processes for providing the shaped porous bodies are also provided, and comprise incorporating into porous body precursors at least one topography-enhancing additive and processing the porous body precursors to provide shaped porous bodies. In those embodiments of the invention wherein the shaped porous bodies comprise alpha-alumina that is desirably fluoride-affected, the process may include exposing the porous body precursors and/or the shaped porous bodies to one or more fluorine-containing species in gaseous form or in the form of one or more gaseous or liquid solutions, suspensions or slurries.

Advantageously, certain of the topography-enhancing additives may at least partially decompose, or otherwise be removed from, the porous body precursors during their processing to form shaped porous bodies, so that while substantial amounts of the additives may not be present, the topographical enhancements may yet be provided to the shaped porous bodies. Other of the topography-enhancing additives that are not so removed or decomposed may be substantially inert in many separation or catalytic applications. Shaped porous bodies comprising the topography-enhancing additives, or prepared from porous body precursors comprising the topography-enhancing additives are thus particularly well-suited for use in many end-use products where any unintended reactivity introduced by other additives may be undesirable.

As such, in a fourth aspect, the present invention contemplates such use, and provides catalysts based upon the shaped porous bodies. More specifically, the catalysts comprise at least one catalytic species deposited on the shaped porous bodies, wherein the shaped porous bodies are prepared from porous body precursors having incorporated therein a topography-enhancing additive. The catalysts and shaped porous bodies need not comprise any amount of the topography-enhancing additive(s), so long as the topography-enhancing effects of the same can be observed. The catalytic species may comprise one or more metals, solid state compounds, molecular catalysts, enzymes or combinations of these. Desirably, the catalysts are suitable for the catalysis of the epoxidation of olefins, preferably alkylenes, more preferably alkylenes comprising from about 2 to about 6 carbon atoms. Most preferably, the catalysts are suitable for the catalysis of the epoxidation of ethylene or propylene, and in these embodiments of the invention, the catalytic species may preferably comprise a silver component. The catalyst may comprise any desired promoters, stabilizers, modifiers or additional additives, such as alkali metals, alkaline earth metals, anion promoters including oxyanions and other anions, manganese components, rhenium components, and/or the efficiency-enhancing salt of a member of a redox-half reaction pair capable of forming a gaseous efficiency enhancing member of a redox-half reaction pair under reaction conditions employing a gaseous nitrogen-containing component, or other promoters known to one of skill in the art, and combinations thereof.

Processes for making the catalysts are also provided and comprise selecting shaped porous bodies prepared from porous body precursors having incorporated therein at least one topography-enhancing additive and depositing at least one catalytic species on the shaped porous bodies. Although the at least one catalytic species may be chosen from metals, solid state compounds, molecular catalysts, enzymes or combinations of these, in preferred embodiments, the catalytic species comprises a silver component. The shaped porous bodies preferably comprise alpha-alumina, and more preferably fluoride-affected alpha-alumina, which effect may be provided by exposure of the shaped porous bodies, or porous body precursors, to a fluorine-containing species, typically provided in gaseous form or in the form of one or more gaseous or liquid solutions, suspensions or slurries.

DESCRIPTION OF THE DRAWINGS

The detailed description of the invention that follows may be further understood and/or illustrated when considered along with the attached drawings.

DETAILED DESCRIPTION OF THE INVENTION

Figure 1:
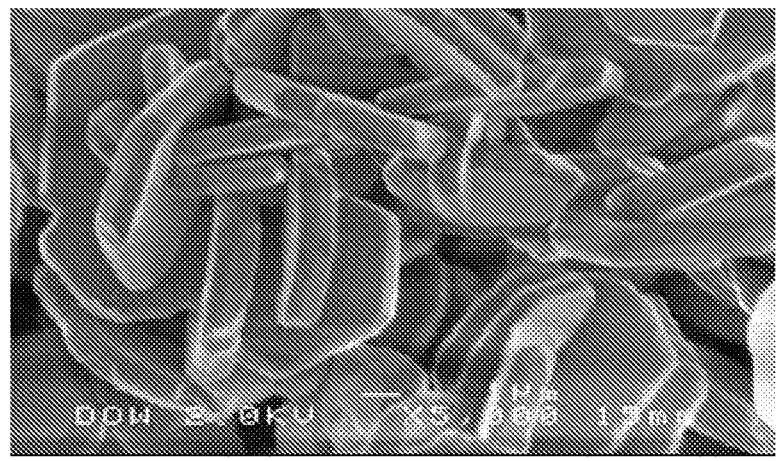
FIG. 1 depicts a scanning electron micrograph of a random sample of the comparative shaped porous body (shaped porous body ID E/comparative) produced in Example 1.

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof, rather, and unless otherwise noted, terms are to be understood according to conventional usage by those of ordinary skill in the relevant art.

As used herein, the phrase 'porous body precursor' is defined as a solid which has been formed into a selected shape suitable for its intended use, and in which shape it will be calcined or otherwise processed or reacted to provide a shaped porous body. The phrase, 'shaped porous body', in turn, is meant to indicate a solid which has been formed into a selected shape suitable for its intended use and has been further processed so as to have a porosity of greater than at least about 10%. As those of ordinary skill in the art are aware, shaped porous bodies may typically be comprised of many, typically thousands, tens of thousands, hundreds of thousands or even millions of smaller particles, and typically, in the present application, it is the surface morphology or aspect ratio of these smaller particles that is observed or measured and referred to herein. As such, it is to be understood that when particular ranges are indicated as advantageous or desired for these measurements, or that a particular surface morphology has been observed, that these ranges may be based upon the measurement or observation of from about 1 to about 10 particles, and although it may generally be assumed that the majority of the particles may thus exhibit the observed morphology or be within the range of aspect ratio provided, that the ranges are not meant to, and do not, imply that 100% of the population, or 90%, or 80%, or 70%, or even 50% of the particles need to exhibit a surface morphology or possess an aspect ratio within this range.

The present invention provides porous body precursors, upon which shaped porous bodies may be based, comprising at least one topography-enhancing additive. Because the topography-enhancing additive is present in the porous body precursors, additional steps are not required in order to add it to the shaped porous bodies and/or end-use products based thereupon, and cost and time savings are provided. In certain especially preferred embodiments, the topography-enhancing additives may advantageously decompose, or otherwise be partially or totally removed during processing of the porous body precursors. The desired topographical improvements may thus be provided, without the shaped porous bodies, or end-use products based thereupon, retaining significant amounts of the topography-enhancing additive(s). As such, any unintended and/or undesired impact on properties of the shaped porous bodies and/or end-use products based thereupon, as may be provided by other modifiers or additives, may be substantially reduced or even avoided.

As used herein, the term 'topography-enhancing additive' is meant to indicate an additive that at least has an impact on one or more topographical properties of the shaped porous bodies prepared from the porous body precursors. Topographical properties include any of those that generally relate to the configuration of the surface of the shaped porous bodies or the particles of which the shaped porous bodies are comprised, e.g., surface area, aspect ratio, pore volume, median pore diameter, surface morphology, etc. 'Surface area', as used herein, refers to the surface area of the shaped porous bodies as determined by the BET (Brunauer, Emmett and Teller) method by nitrogen as described in the Journal of the American Chemical Society 60 (1938) pp. 309-316. 'Aspect ratio' means the ratio of the longest or major dimension to the smallest or minor dimension of the particles of which the shaped porous bodies are comprised, determined by examination of the scanning electron micrograph of the shaped porous body. 'Pore volume' (also, 'total pore volume' or 'porosity') means pore volume of the shaped porous body and is typically determined by mercury porosimetry. The measurements reported herein used the method described in Webb & Orr, Analytical Methods in Fine Particle Technology (1997), p. 155, using mercury intrusion to 60,000 psia using Micrometrics Autopore IV 9520, assuming 130° contact angle, 0.473 N/M surface tension of Hg. 'Median pore diameter' means the pore diameter corresponding to the point in the pore size distribution at which half of the cumulative pore volume of the shaped porous bode has been measured, and 'surface morphology' means the physical structure of the surface of the particles of which the shaped porous body is comprised, typically observed by scanning electron microscopy (SEM).

Certain of the topography-enhancing additives may advantageously at least partially, or substantially entirely, decompose, or otherwise be removed from the porous body precursors when they are processed to provide the shaped porous bodies. These topography-enhancing additives thus exert their effect, without yet being present to potentially interfere in any reactions or separations in which end-use products based upon the porous body precursors and/or shaped porous bodies may ultimately be used. That is, since the topography-enhancing additives are present when the porous body precursors and perhaps shaped porous bodies are formed, they can impact the topographical properties thereof, either merely by their presence or perhaps by undergoing phase transitions that assist in the formation of the desirable topographical properties. Thereafter, certain, but not necessarily all, of the topography-enhancing additive(s) may be decomposed or otherwise reduced or eliminated by the porous body precursor and/or shaped porous body processing conditions.

Any additive capable of providing advantageous or desired topographical effects to the shaped porous bodies may be employed in the porous body precursors. It is understood that desired topographical effects will depend upon the desired application of the shaped porous bodies, and so for some applications, a smaller, e.g., pore volume, or particular surface morphology may be desired, and any additive capable of achieving the enhanced effect, whether the enhancement be a relative increase or decrease, is considered to be a topography-enhancing additive.

Any solid, liquid or gaseous composition comprising at least one silicon containing species is thought to be capable of providing enhanced topographical effects to porous body precursors into which it is incorporated, or shaped porous bodies or end-use products based upon the same, and is suitable for use as a topography-enhancing additive according to the present invention. For example, the topography-enhancing additive(s) may be colloidal silica, tetraethyl orthosilicate (TEOS), pure silicon, silicon ceramides, silicon containing oils or polymers, $SiF_4$, $SiCl_4$, natural or synthetic silicates (including olivines, sheet-like micas, quartz, feldspars, spinels, pyroxenes, and the like), siloxanes such as tetremethylsiloxane, or combinations of these. Of these colloidal silica, TEOS, natural or synthetic silicates, and gaseous silicone-containing species such as $SiF_4$, $SiCl_4$ and tetramethylsiloxane, are preferred.

Colloidal silicas are suspensions of fine sized, i.e., less than 150 nm, amorphous, nonporous silica particles in liquid phase. Typically colloidal silicas exhibit particle densities in the range of 2.1 to 2.3 g/cc, and may either be monodisperse or polydisperse suspensions. Advantageously, the inclusion of colloidal silica in the porous body precursors can provide the particles of the shaped porous bodies based thereupon with a unique eight, ten or even twelve-sided surface morphology, or, may round the edges of the particles of the shaped porous bodies and increase their aspect ratio compared to particles of the shaped porous bodies without colloidal silica. Such morphologies are advantageous not only because they generally provide the particles with a greater surface area, but also because they may provide for increased interconnections between the particles of the shaped porous bodies, thus also adding to the overall strength of the shaped porous bodies. In these embodiments, the shaped porous bodies may have a measured surface area of at least about 0.7 $m^2/g$, or even about 2.0 $m^2/g$, or up to about 3.0 $m^2/g$. Shaped porous bodies comprising colloidal silica may also comprise particles that exhibit an enhanced aspect ratio as compared to the particles that make up shaped porous bodies without colloidal silica, or aspect ratios of at least about 5, or even about 50, or up to about 75.

Other examples of topography-enhancing additives according to the invention include natural or synthetic silicates, such as pyroxenes. Pyroxenes have the general formula $XY(Si,Al)_2O_6$ where X may be calcium, sodium, iron$^{+2}$, magnesium, zinc, manganese or lithium and Y may be ions of smaller size, such as chromium, aluminium, iron$^{+3}$, magnesium, manganese, scandium, titanium, vanadium, or iron$^{+2}$. Accepted nomenclature for pyroxenes is given in Canadian Mineralogist, Vol. 27, pp. 143-156 (1989), incorporated herein by reference in its entirety for any and all purposes. Any pyroxene of the formula $XY(Si,Al)_2O_6$ can be utilized and non-limiting examples of these include clinoenstatite, clinoferrosilite, kanoite, pigeonite, diopside, hedenbergite, johannsenite, petedunnite, augite, omphacite, esseneite, spodumene, jadeite, aegirine, ferrosilite, jervisite, donpeacorite, aegirine-augite, kosmochloror combinations thereof.

Of these, spodumene ($LiAlSi_2O_6$) is preferred, and in those embodiments of the invention wherein the topography-enhancing additive comprises the same, the particles of the shaped porous bodies may exhibit enhanced aspect ratios, or aspect ratios of at least 5, or even about 50, or up to about 75. Advantageously, the inclusion of spodumene in the porous body precursors can provide at least a portion of the particles of the shaped porous bodies based thereupon with a unique eight, ten or even twelve-sided surface morphology, may round the edges of the particles of the shaped porous bodies and/or increase the aspect ratio of particles of the shaped porous bodies as compared to the particles of shaped porous bodies without spodumene. Enhanced aspect ratios may provide increases in surface area, as well as interconnections between the particles of the shaped porous bodies, and thus overall increases in strength of the shaped porous bodies. In these embodiments, the shaped porous bodies may have measured surface areas of at least about 0.7 $m^2/g$, or even about 2.0 $m^2/g$, or up to about 3.0 $m^2/g$.

Gaseous silicon species may also be utilized as the at least one topography enhancing additive according to the invention, and advantageously may further reduce processing time, as rather than mixing the gaseous silicon species with other desired materials of the porous body precursors, the porous body precursors may simply be exposed to gases, or gaseous solutions, comprising a silicon-containing species. Any gas, or gaseous solution, comprising a silicon-containing species is thought to be capable of providing topography enhancements to the porous body precursor, shaped porous bodies and/or end-use products based thereupon, and non-limited examples of these include $SiF_4$, $SiCl_4$ and gaseous siloxanes, such as tetra methylsiloxane.

While the invention is not constrained by any particular theory, the inclusion of the topography-enhancing additive may result in the generation of a silicon-containing species upon processing of the porous body precursors or shaped porous bodies that, in turn, unexpectedly influences the rate of conversion of transition alumina to alpha-alumina and can result in shaped porous bodies having more desirable topography, e.g., surface area, pore volume, etc., than in the case where these topography-enhancing additives are not added. Topography-enhancing additives that may undergo structural and/or phase transformations in the temperature range at which the transition alumina or transition alumina precursors of porous body precursors comprising the same are being converted to alpha-alumina, are preferred as it is thought that such topography-enhancing additive(s) may have a larger impact on the resulting shaped porous body topography. Non-limiting examples of these include natural or synthetic silicates, and preferred silicates for use in these embodiments of the invention include the pyroxenes, and spodumene is further a particularly preferred pyroxene.

Any amount of the topography-enhancing additives may be included in the inventive porous body precursors. Especially in those instances where the topography-enhancing additive is substantially decomposed or otherwise removed during processing of the porous body precursors to provide the shaped porous bodies of the invention, the amount thereof to be included in the porous body precursors may only be limited by cost and/or manufacturing practicality. That is, practicality dictating that only as much of the topography-enhancing additives should be used to achieve the maximum effect, and not so much as to unnecessarily add to the cost, or detrimentally impact the processability of the porous body precursors.

That being said, the topography-enhancing additives of the present invention advantageously can exert their effects in surprisingly low amounts, and it is expected that amounts of less than 10 weight percent (wt %) based upon the total weight of the porous body precursor, or less than 5 wt %, or even less than 3 wt % will be required to provide appreciable enhancements.

In addition to the topography-enhancing additive(s), the porous body precursors may comprise any of the large number of porous refractory structure or support materials, so long as whatever the porous refractory material chosen, it is relatively inert in the presence of the chemicals and processing conditions employed in the application in which the shaped porous body will be utilized. In many end use applications, the chosen support material may also desirably have a porous structure and a relatively high surface area. For example, in those embodiments of the invention where the shaped porous bodies are desirably used as the basis of catalysts, it may be important for the shaped porous bodies to be of a physical form and strength to allow the desired flow of reactants, products and any required ballast through the reactor, while also maintaining their physical integrity over the life of the catalyst. In these embodiments of the invention, significant breakage or abrasion may result in undesirable pressure drops within the reactor, and are desirably avoided. It may also be important that the shaped porous bodies, and catalysts based upon the same, be able to withstand fairly large temperature and pressure fluctuations within the reactor.

The porous body precursors may comprise, for example, any of the transition alumina precursors, transition aluminas, hydrated aluminium compounds, alpha-alumina, silicon carbide, silicon dioxide, zirconia, zirconium silicate, graphite, magnesia and various clays. The use of transition alumina precursors, transition aluminas, or other alpha-alumina precursors, is preferred, as they may at least partially be converted to transition aluminas, or alpha-alumina, respectively, during processing. Generally, in those embodiments of the invention wherein the porous body precursors and shaped porous bodies are intended for end use as catalyst supports, mixtures of hydrated aluminum compounds, such as boehmite, gibbsite, or bayerite, or transition aluminas obtained by thermal dehydration of the hydrated aluminum compounds, may be suitable. Preferred alpha-alumina precursors in these embodiments of the invention comprise pseudo-boehmite, gibbsite, gamma-alumina and kappa-alumina.

As used herein, 'transition alumina precursors' are one or more materials that, upon thermal treatment, are capable of being at least partially converted to transition alumina. Transition alumina precursors include, but are not limited to, aluminum tri-hydroxides, such as gibbsite, bayerite, and nordstrandite; and aluminum oxide hydroxides, such as boehmite, pseudo-boehmite and diaspore. 'Transition aluminas' are one or more aluminas other than alpha-alumina, which are capable of being at least partially converted to alpha-alumina under thermal treatment at 900° C. or greater. Transition aluminas possess varying degrees of crystallinity, and include, but are not limited to gamma-alumina, delta-alumina, eta-alumina, kappa-alumina, chi-alumina, rho-alumina, and theta-alumina. "Alpha-alumina precursor" means one or more materials capable of being transformed into alpha-alumina, including transition alumina precursors and transition aluminas.

In certain end-use products, e.g., catalysts, it can be advantageous for the porous body precursors to comprise a material that is not only compositionally pure, but also phase pure, or capable of being converted to phase pure material with appropriate processing. As used herein, the phrase 'compositionally pure' is meant to indicate a material that is substantially a single substance, with only trace impurities being present. On the other hand, the phrase 'phase pure' is meant to indicate a homogeneity in the phase of the material. For example, if the porous body precursors comprise transition alumina precursors, or transition aluminas, that are converted to alpha-alumina during processing to provide the shaped porous bodies, a high phase purity would indicate that the transition aluminas had been converted so that the shaped porous body comprises at least about 90%, or at least 95%, or even about 98% alpha-alumina phase purity (i.e., alpha-alumina). In those applications where such a phase purity is desired, the porous body precursors may desirably comprise one or more transition alumina precursors or transition aluminas. However, the invention is not so limited and the shaped porous body may comprise any combination of transition alumina precursors, transition aluminas and alpha-alumina.

The porous body precursors of the invention may comprise any other components, in any amounts, necessary or desired for processing, such as, e.g., water, acid, binders, pore formers, dopants, etc., of common knowledge to those of ordinary skill in the art of the production of shaped porous bodies for use as structures or supports. In those embodiments of the invention wherein the porous body precursors are intended for use in shaped porous bodies that will ultimately be used in catalytic applications, and comprise transition alumina precursors or transition aluminas, the porous body precursors may also contain precursor catalyst compounds that have elements that may desirably be incorporated onto the surface or into the lattice structure of the alpha-alumina particles that will be formed upon processing of the porous body precursors to form shaped porous bodies. Examples of compounds useful for forming these incorporated catalysts include inorganic and organic compounds that form catalysts such as metals, metal oxides, metal carbides and organo-metallic compounds.

The topography-enhancing additives identified herein may prove so effective at imparting their enhancements, that the use of additional dopants, pore formers, etc, typically employed to achieve similar topographical enhancements, may be reduced or substantially avoided. Nonetheless, if the same is desired or required, the porous body precursors may also comprise other organic compounds (e.g., binders and dispersants, such as those described in *Introduction to the Principles of Ceramic Processing*, J. Reed, Wiley Interscience, 1988) to facilitate the shaping, or to alter the porosity, of the porous body precursors and/or shaped porous bodies. Pore formers (also known as burn out agents) are materials used to form specially sized pores in the shaped porous bodies by being burned out, sublimed, or volatilized. Pore formers are generally organic, such as ground walnut shells, granulated polyolefins, such as polyethylene and polypropylene, but examples of inorganic pore formers are known. The pore formers are usually added to the porous body precursor raw materials prior to shaping. During a drying or calcining step or during the conversion of the alpha-alumina precursor to alpha-alumina, the pore formers may typically be burned out, sublimed, or volatilized.

Modifiers may also be added to the porous body precursor raw materials or the porous body precursors to change the chemical and/or physical properties of the shaped porous bodies or end-use products based upon the shaped porous bodies. If inclusion of the same is desired or required, any chosen modifier(s) can be added during any stage of the process, or at one or more steps in the process. For example, a metal oxide modifier can be added to the porous body precursor raw materials prior to, or after, the mixing/mulling step, prior to, or after, formation of the porous body precursors into formed porous body precursors, or before or after drying, or other thermal processing of the shaped porous bodies.

As used herein, "modifier" means a component other than the porous refractory material and topography-enhancing additive, added to a porous body precursor or shaped porous body to introduce desirable properties such as improved end-use performance. More particularly, modifiers can be inorganic compounds or naturally occurring minerals which are added in order to impart properties such as strength and, in some cases, change the surface chemical properties of the shaped porous bodies and/or end-use products based thereupon.

Whatever the raw materials selected for use in the porous body precursors, they are desirably of sufficient purity so that there are limited reactions between any of them. In particular, the topography-enhancing additives should be of sufficient purity so that any impurities are not present in a quantity sufficient to substantially detrimentally impact the properties of the porous body precursors, shaped porous bodies and/or catalysts, i.e., any impurities are desirably limited to not more than 3 wt %, or even not more than 1.5 wt %, of the total weight of the porous body precursors.

The desired components of the porous body precursors, i.e., at least the chosen porous refractory material and the at least one topography-enhancing additive, may be combined by any suitable method known in the art. Further, the topography-enhancing additive and other raw materials may be in any form, and combined in any order and the order of addition of the topography-enhancing additive to the other raw materials is not critical. Examples of suitable techniques for combining the porous body precursor materials include ball milling, mix-mulling, ribbon blending, vertical screw mixing, V-blending, and attrition milling. The mixture may be prepared dry (i.e., in the absence of a liquid medium) or wet. Additionally, the porous refractory material may have the at least one topography-enhancing additive incorporated therein via exposure to a gas, or gaseous or liquid solution, suspension or slurry, comprising a silicon-containing species.

For example, in those embodiments of the invention wherein the topography-enhancing additive comprises a gas, or gaseous solution comprising a silicon-containing species, the porous body precursors may be placed in a vessel and heated to a first temperature in the range of about 850° C. to about 1150° C. Once within this temperature range, the gas or gaseous solution comprising a silicon-containing species may be introduced into the vessel, and the vessel heated to a second temperature greater than the first temperature and between about 950° C. and about 1150° C. to effectuate the incorporation of the topography-enhancing additive into the porous body precursors. Desirably, in these embodiments of the invention, the first temperature is increased to the second temperature at a rate of about 0.2° C. to about 4° C. per minute. In those embodiments of the invention wherein porous body precursors comprise transition aluminas desirably converted substantially entirely to fluoride-affected alpha-alumina, a gas or gaseous solution comprising a fluorine-containing species may be introduced before, after, or simultaneously therewith the gas or gaseous solution comprising a silicon-containing species, and in fact, in some embodiments of the invention, a single gas or gaseous solution may comprise both the fluorine and the silicon species, as is the case with, e.g., $SiF_4$.

Once mixed, the porous body precursor raw materials may be formed by any suitable method, such as e.g., injection molding, extrusion, isostatic pressing, slip casting, roll compaction and tape casting. Each of these is described in more detail in *Introduction to the Principles of Ceramic Processing*, J. Reed, Chapters 20 and 21, Wiley Interscience, 1988, incorporated herein by reference. Suitable shapes for formed porous body precursors will vary depending upon the end use of the same, but generally can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls), cylinders having gas channels from side wall to side wall, cylinders having two or more gas channels, and ribbed or finned structures. If cylinders, the porous body precursors may be circular, oval, hexagonal, quadrilateral, or trilateral in cross-section. In those embodiments of the invention wherein the porous body precursors are used to prepare shaped porous bodies intended for end use as catalysts, the porous body precursors may desirably be formed into a rounded shape, e.g., pellets, rings, tablets and the like, having diameters of from about 0.1 inch (0.25 cm) to about 0.8 inch (2 cm).

The porous body precursors so formed may then optionally be heated under an atmosphere sufficient to remove water, decompose any organic additives, or otherwise modify the porous body precursors prior to introduction into a kiln, oven, pressure-controlled reaction vessel or other container for any further required processing into shaped porous bodies. Suitable atmospheres include, but are not limited to, air, nitrogen, argon, hydrogen, carbon dioxide, water vapor, those comprising fluorine-containing species or combinations thereof. The atmosphere may also comprise a silicone-containing species, especially in those embodiments of the invention wherein a gas or gaseous solution comprising a silicon-containing species is desirably utilized as the topography-enhancing additive.

Before or during calcination, and in those embodiments of the invention wherein the porous body precursors comprise one or more transition alumina precursors, transition aluminas, or other alpha-alumina precursors, the porous body precursors and/or shaped porous bodies may desirably be fluoride affected, as may be achieved by exposing the porous body precursors and/or shaped porous bodies to fluorine-containing species, as may be provided in gaseous form, in gaseous liquid solution, or via the provision of solid fluorine-containing source operatively disposed relative to the porous body precursors and/or shaped porous bodies. For advantages provided in processing, any such fluoride effect may desirably be achieved via exposure of the porous body precursors and/or shaped porous bodies to one or more fluorine-containing species in gaseous form or in gaseous solution. The particulars of such gaseous fluoride affectation are described in copending, commonly assigned PCT application no. PCT/US2006/016437, the entire disclosure of which is hereby incorporated by reference herein for any and all purposes.

One preferred method of providing the fluoride effect to the porous body precursors or shaped porous bodies comprises heating a vessel containing formed porous body precursors comprising the at least one topography-enhancing additive to a temperature of from about 750° C. to about 1150° C., preferably from about 850° C. to about 1050° C. A fluorine-containing gas is then introduced into the vessel and can establish a partial pressure within the vessel of between about 1 torr and about 10,000 torr. The partial pressure may be 1, 100, 200, 300, 400, 500, 600, 700, 800, 900, 1000, 2500, 5000, 7500, or 10,000 torr or pressures in between. Preferred partial pressures are below about 760 torr. The porous body precursors are allowed to be in contact with the fluorine-containing gas for a time of about 1 minute to about 48 hours. The time may be 1 minute, 15 minutes, 30 minutes, 45 minutes, 1 hour, 90 minutes, 2 hours, 3 hours, 4 hours, 5 hours, 10 hours, 20 hours, 30 hours, 40 hours or about 48 hours or any amount of time in between. Shorter times for contacting the gas with the porous body precursors are preferred, with times of from about 30 minutes to about 90 minutes being particularly preferred. Of course, and as those of ordinary skill in the art can readily appreciate, the preferred combinations of time and temperature and/or pressure vary with the fluorine-containing gas used, the topography-enhancing additive added to the porous body precursors, and the other components of the porous body precursors.

One particularly preferred method of providing a fluoride effect to porous body precursors comprising one or more transition alumina precursors, transition aluminas or other alpha-alumina precursors, comprises heating a vessel containing the porous body precursors to a first temperature in the range of about 850° C. to about 1150° C. prior to introducing the fluorine-containing gas and then heating to a second temperature greater than the first temperature and between about 950° C. and about 1150° C. after introducing the fluorine-containing gas. Desirably, in these embodiments of the invention, the first temperature is increased to the second temperature at a rate of about 0.2° C. to about 4° C. per minute. Whatever time and temperature combination utilized, at least 50% of the transition alumina precursors, transition aluminas or other alpha-alumina precursors are desirably converted to alpha-alumina platelets.

Another particular method for preparing porous body precursors suitable for the preparation of shaped porous bodies desirably comprising fluoride-affected alpha-alumina comprises mixing the topography-enhancing additive with boehmite alumina (AlOOH) and/or gamma-alumina, peptizing the mixture with a composition containing an acidic component and halide anions (preferably fluoride anions), then forming (e.g., by extruding or pressing) the mixture to provide porous body precursors, and then drying and calcining the porous body precursors at temperatures between 1000° C. and 1400° C. for a time between 45 minutes and 5 hours to provide shaped porous bodies comprising fluoride-affected alpha-alumina.

Shaped porous bodies comprising alpha-alumina according to the invention will desirably have measured surface areas of at least about 0.5 m$^2$/g (more preferably from about 0.7 m$^2$/g to about 10 m$^2$/g), a measured pore volume of at least about 0.5 cc/g (more preferably from about 0.5 cc/g to about 2.0 cc/g), purity (exclusive of the at least one topography-enhancing additive) of at least about 90 percent alpha-alumina particles, more preferably at least about 95 percent alpha-alumina particles, and even more preferably at least about 99 weight percent alpha-alumina particles, the shaped porous bodies also desirably having a median pore diameter from about 1 to about 50 microns. Further, the shaped porous bodies according to the invention will desirably be comprised largely of particles in the form of platelets having at least one substantially flat major surface having a lamellate or platelet morphology, at least 50 percent of which (by number) have a major dimension of less than about 50 microns. As used herein, the term "platelet" means that a particle has at least one substantially flat major surface, and that some of the particles have two, or sometimes more, flat surfaces. The "substantially flat major surface" referred to herein may be characterized by a radius of curvature of at least about twice the length of the major dimension of the surface.

Otherwise, the shaped porous bodies may comprise any suitable shape, as will depend upon the end use of the same.

Generally suitable shapes for the shaped porous bodies can include without limitation pills, chunks, tablets, pieces, spheres, pellets, tubes, wagon wheels, toroids having star shaped inner and outer surfaces, cylinders, hollow cylinders, amphora, rings, Raschig rings, honeycombs, monoliths, saddles, cross-partitioned hollow cylinders (e.g., having at least one partition extending between walls), cylinders having gas channels from side wall to side wall, cylinders having two or more gas channels, and ribbed or finned structures. If cylinders, the shaped porous bodies may be circular, oval, hexagonal, quadrilateral, or trilateral in cross-section. In those embodiments of the invention wherein the shaped porous bodies are used to prepare catalysts, the shaped porous bodies may desirably be formed into a rounded shape, e.g., pellets, rings, tablets and the like, having diameters of from about 0.1 inch (0.25 cm) to about 0.8 inch (2 cm).

Because of their advantageous, enhanced topographical properties, the shaped porous bodies provided by the invention are particularly well suited for incorporation into many end-use applications. More particularly, shaped porous bodies of the invention can exhibit enhanced pore volumes and surface areas, and be comprises of particles that exhibit enhanced aspect ratios and/or surface morphology, and so are well suited for use as, e.g., catalyst supports, filters, membrane reactors and preformed bodies for composites. As used herein, "carrier" and "support" are interchangeable terms. A carrier provides surface(s) to deposit, for example, catalytic metals, metal oxides, or promoters that are components of a catalyst.

If used as catalyst supports, the shaped porous bodies may advantageously be used as supports for catalysts useful for the epoxidation of alkenes, partial oxidation of methanol to formaldehyde, partial selective oxidation of saturated hydrocarbons to olefins, selective hydroformylation of olefins, selective hydrogenations, selective hydrogenation of acetylenes in cracked hydrocarbon streams, selective hydrogenation of di-olefins in olefin-di-olefin-aromatic streams also known as pyrolysis gasoline, and selective reduction of $NO_x$ to $N_2$. Other catalytic applications for the present shaped porous bodies include as carriers for automotive exhaust catalysts for emissions control and as carriers for enzymatic catalysis. In addition to end-use applications as catalytic supports, the inventive shaped porous bodies may also be used for the filtration of materials from liquid or gas streams, see, e.g. Auriol, et al., U.S. Pat. No. 4,724,028. In these applications the shaped porous bodies may either be the discriminating material, or may be the carrier for the discriminating material. Other uses for the present shaped porous bodies include, but are not limited to, as packing for distillations and catalytic distillations.

Indeed, due to the numerous advantages imparted by the inventive shaped porous bodies to this particular end use, in one embodiment of the invention, the shaped porous body is used as the basis of a catalyst and these catalysts as well as the processes for making them are also provided. Typically, such processes include at least depositing one or more catalytic species on the shaped porous bodies. Once deposited, the catalytic species can be bound directly on the surface of the shaped porous bodies of the invention, or, the catalytic species may be bound to a washcoat, i.e., another surface which has been applied to the surface of the shaped porous bodies. The catalytic species may also be covalently attached to a macromolecular species, such as synthetic polymer or a biopolymer such as a protein or nucleic acid polymers, which in turn, is bound either directly to the surface of the shaped porous bodies or a washcoat applied thereto. Further, a deposited catalytic species may reside on the surface of the shaped porous bodies, be incorporated into a lattice provided on the surface of the shaped porous bodies, or be in the form of discrete particles otherwise interspersed among the shape porous bodies.

If the shaped porous bodies are desirably used as supports for catalysts, any catalytic species may be deposited thereupon. Non-limiting examples of catalytic species that may advantageously be supported by the shaped porous bodies include metals, solid state compounds, molecular catalysts, enzymes and combinations of these.

Metals capable of exhibiting catalytic activity include noble metals, e.g. gold, platinum, rhodium, palladium, ruthenium, rhenium, and silver; base metals such as copper, chromium, iron, cobalt, nickel, zinc, manganese, vanadium, titanium, scandium, and combinations of these. Solid state compounds suitable for use as catalytic species include, but are not limited to, oxides, nitrides and carbides, and one particular example of a class of solid state compounds useful as a catalytic species are the perovskite-type catalysts that comprise a metal oxide composition, such as those described by Golden, U.S. Pat. No. 5,939,354, incorporated herein by reference. Exemplary molecular catalytic species include at least metal Schiff base complexes, metal phosphine complexes and diazaphosphacycles. Non-limiting examples of enzymes useful as catalytic species include lipases, lactases, dehalogenases or combinations of these, with preferred enzymes being lipases, lactases or combinations thereof.

The desired catalytic species may be deposited on the shaped porous bodies according to any suitable method, to provide catalysts according to the invention. Typically, metal catalytic species are conveniently applied by solution impregnation, physical vapor deposition, chemical vapor deposition or other techniques. Molecular and enzymatic catalysts may typically be provided onto the shaped porous bodies via covalent attachment directly to the shaped porous bodies, to a wash coat (such as silica, alumina, or carbon) or supported high surface area carbon (such as carbon nanotubes) applied thereto. Enzyme catalysts may also be supported by other supports known in the art, including the carbon nanofibers such as those described by Kreutzer, WO2005/084805A1, incorporated herein by reference, polyethylenimine, alginate gels, sol-gel coatings, or combinations thereof. Molecular catalyst may also be immobilized on the surface(s) of the shaped porous bodies by any of the immobilization generally known to those skilled in the art, such as attachment through silane coupling agents.

The amount of catalytic species may be any suitable amount depending on the particular catalytic species and application, and those of ordinary skill in the catalyst manufacturing art are well equipped to make this determination based upon their knowledge and information in the public arena. Very generally speaking then, typically, at least about 10 percent to essentially all of the shaped porous bodies may be coated with, or otherwise contain, catalytic species.

One particularly preferred class of catalysts according to the invention are those useful for the epoxidation of olefins. In olefin epoxidation, a feed containing an olefin and oxygen is contacted with a catalyst under epoxidation conditions, causing the olefin to react with oxygen to form an olefin oxide. The resulting product mix contains the olefin oxide, as well as any unreacted feed and other combustion products, such as carbon dioxide. The olefin oxide so produced may be reacted with water, alcohol or amines, for example, to produce diols, diol ethers or alkanolamines, respectively.

Ethylene glycol in particular is used in two significant applications: as a raw material for poly(ethylene terephthalate) for use in polyester fiber, film, and containers, and as an automotive antifreeze. Di-, tri-, and tetraethylene glycols are coproducts of ethylene glycol. Ethylene glycol can be produced by the (catalyzed or uncatalyzed) hydrolysis of ethylene oxide. Ethylene oxide hydrolysis proceeds with either acid or base catalysis or uncatalyzed in neutral medium. Acid-catalyzed hydrolysis activates the ethylene oxide by protonation for the reaction with water. Base-catalyzed hydrolysis results in considerably lower selectivity to ethylene glycol. A principal by-product is diethylene glycol and higher glycols, triethylene and tetraethylene glycols, are also produced. Ethylene glycol monoethers can be manufactured by reaction of an alcohol with ethylene oxide. Ethanolamine can be manufactured by the reaction of ethylene oxide with ammonia. See, e.g., U.S. Pat. No. 4,845,296, which is incorporated herein by reference.

One particular example of an olefin epoxidation of commercial importance is the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, $4^{th}$ Ed. (1994) Volume 9, pages 915-959, all of which are incorporated by reference herein in their entirety for any and all purposes. Although the invention is not so limited, for purposes of simplicity and illustration, catalysts according to the invention useful in olefin epoxidations will be further described in terms of, and with reference to, the epoxidation of ethylene.

Catalysts are a very important factor in the commercial viability of such epoxidation reactions. The performance of catalysts in these reactions is typically evaluated on the basis of the catalysts' selectivity, activity, and stability during the epoxidation reactions. Selectivity is commonly understood to be the molar percentage of the converted olefin yielding the desired olefin oxide, while stability typically refers to how the selectivity or activity of the process changes during the time that a particular batch of catalyst is being used, i.e., as more olefin oxide is produced. Catalysts based upon the porous body precursors and shaped porous bodies of the present invention are expected to provide advantages in selectivity, activity and/or stability resulting from one or more property changes provided by inclusion of the topography-enhancing additives in the porous body precursors.

In these embodiments of the invention in particular, a high purity shaped porous body is highly desirable. For these applications, a porous body precursor consisting essentially of one or more alpha-alumina precursors is preferred, and shaped porous bodies based thereupon will desirably comprise at least about 90 percent alpha-alumina platelets, more preferably at least about 95 percent alpha-alumina platelets, and even more preferably at least about 99 percent alpha-alumina platelets exclusive of the topography-enhancing additive.

One method of obtaining such a shaped porous body precursor is to extrude a mixture comprising an alpha-alumina precursor (e.g. pseudo-boehmite or gibbsite), at least one topography-enhancing additive (e.g., colloidal silica and/or one or more pyroxenes), an organic binder (e.g. methylcellulose), an organic lubricant (e.g. polyethylene glycol) and, optionally, an organic pore former (e.g. nut shell flour, polypropylene or polyethylene fibers or powders) followed by cutting, drying and debindering/calcining in air.

In other epoxidation catalyst applications, and in addition to the topography-enhancing additives, or further exemplary of the additional components or modifiers discussed hereinabove, a primarily alpha-alumina shaped porous body having minor oxide components containing alkaline earth metal, transition metal, rare earth or main group elements is highly desirable. Such shaped porous bodies are within the scope of this invention, and can readily be achieved by the processes provided herein, by adding the desired minor components as pure oxides or salts, or if desired as mixed oxides or salts, to the porous body precursors, or by adding the minor components via either solution or gas phase infiltration during processing of the porous body precursors to provide the shaped porous bodies. Common additives for formation of minor phases giving improved catalyst performance in ethylene epoxidation reactions include borates, alkaline earth metal containing compounds, transition metal element-containing compounds, rare earth element-containing compounds, and main group element-containing compounds.

Shaped porous bodies suitable for end-use application as the basis for ethylene epoxidation catalysts according to the invention may take any of the shapes suitable for carriers or supports, discussed above. Conventional commercial fixed bed ethylene oxide reactors are typically in the form of a plurality of parallel elongated tubes (in a suitable shell) having an outer diameter of from about 1 inches to about 3 inches (2.5 to 7.5 cm) and a length of from about 15 feet to about 45 feet (4.5 to 13.5 m). For use in such fixed bed reactors, the shaped porous bodies will desirably be formed into a rounded shape, such as, for example, spheres, pellets, rings, tablets, and the like, having diameters from about 0.1 inch (0.25 cm) to about 0.8 inch (2 cm).

Catalysts according to this embodiment of the invention may be prepared by impregnating the inventive shaped porous bodies with a solution of one or more silver compounds, or otherwise depositing the silver throughout the pores of the shaped porous bodies and reducing the silver compound as is well known in the art. See for example, Liu, et al., U.S. Pat. No. 6,511,938 and Thorsteinson et al., U.S. Pat. No. 5,187,140, incorporated herein by reference.

Generally, the shaped porous bodies are impregnated with a catalytic amount of silver, which is any amount of silver capable of catalyzing the direct oxidation of, e.g., ethylene, with oxygen or an oxygen-containing gas to the corresponding alkylene oxide. Typically, the shaped porous bodies are impregnated with one or more silver compound solutions sufficient to allow the silver to be provided on the shaped porous bodies in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Although the amount of silver utilized is not particularly limited, the amount of silver provided in connection with the shaped porous bodies may usually be less than about 70 percent, and more preferably, less than about 50 percent by weight, based on the weight of the catalysts.

Although silver particle size in the finished catalysts is important, the range is not narrow. A suitable silver particle size can be in the range of from about 10 angstroms to about 10,000 angstroms in diameter. A preferred silver particle size ranges from greater than about 100 angstroms to less than about 5,000 angstroms in diameter. It is desirable that the silver be relatively uniformly dispersed within, throughout, and/or on the shaped porous body.

As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

There are at least two types of promoters—solid promoters and gaseous promoters. A solid promoter may conventionally be incorporated into the inventive catalysts prior to their use, either as a part of the shaped porous bodies, or as a part of the silver component applied thereto. Examples of well-known solid promoters for catalysts used to produce ethylene oxide include compounds of potassium, rubidium, cesium, rhenium, sulfur, manganese, molybdenum, and tungsten. Examples of solid promoter and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference in their entirety for any and all purposes.

Gaseous promoters, on the other hand, are gas-phase compounds or mixtures thereof which are introduced into a reactor, either alone or with other gas phase reactants, before or during the process desirably catalyzed. Gas phase promoters can desirably further enhance the performance of the catalyst, and may do so either alone, or may work in conjunction with one or more solid promoters. Halide-containing components, e.g., chlorine-containing components, may typically be employed as gaseous promoters in processes involving the epoxidation of alkylenes. See, for example, Law, et al., U.S. Pat. Nos. 2,279,469 and 2,279,470, each incorporated herein by reference in their entirety for any and all purposes.

Gaseous promoters capable of generating at least one efficiency-enhancing member of a redox half reaction pair may also be used, and one example of such a gaseous promoter would be any of those comprising a nitrogen-containing component. See, for example, Liu, et al., U.S. Pat. No. 6,511,938 particularly at column 16, lines 48 through 67 and column 17, line 28, and Notermann, U.S. Pat. No. 4,994,589, particularly at column 17, lines 10-44, each incorporated herein by reference in their entirety for any and all purposes. Alternatively, a suitable precursor compound may also be added such that the desired amount of the salt of a member of a redox-half reaction pair is formed in the catalyst under epoxidation conditions, especially through reaction with one or more of the gas-phase reaction components. The suitable range of concentrations of the precursor of the efficiency enhancing promoter is the same as for the salt. As used herein, the term "salt" does not indicate that the anion and cation components of the salt be associated or bonded in the solid catalyst, but only that both components be present in some form in the catalyst under reaction conditions.

Solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" referring to a positively charged moiety and "anionic" or "anion" referring to a negatively charged moiety. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst.

Once incorporated into the catalyst, and/or during the reaction to make ethylene oxide, the specific form of the promoter on the catalyst may be unknown, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or use. Oxyanions, or precursors to oxyanions, may be converted to a cationic or covalent form. In many instances, analytical techniques may not be sufficient to precisely identify the species present. The invention is not intended to be limited by the exact species that may ultimately exist on the catalyst during use and simply for the sake of ease of understanding, the solid promoters will be referred to in terms of cations and anions regardless of their form in the catalyst under reaction conditions.

The catalyst prepared on the inventive shaped porous bodies may contain alkali metal and/or alkaline earth metal as cationic promoters. Exemplary of the alkali metal and/or alkaline earth metals are lithium, sodium, potassium, rubidium, cesium, beryllium, magnesium, calcium, strontium and barium. Other cationic promoters include Group 3b metal ions including lanthanide series metals. In some instances, the promoter may comprise a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst, if desirably included therein, is not narrow and may vary over a wide range. The optimum alkali metal promoter concentration for a particular catalyst will be dependent upon performance characteristics, such as catalyst efficiency, rate of catalyst aging and reaction temperature. More particularly, the concentration of alkali metal (based on the weight of cation, for example cesium) in the finished catalysts of the present invention may vary from about 0.0005 to 1.0 wt. %, preferably from about 0.005 to 0.5 wt. %. The preferred amount of cation promoter deposited on or present on the surface of the shaped porous body or catalyst generally lies between about 10 ppm and about 4000 ppm, preferably between about 15 ppm and about 3000 ppm, and more preferably between about 20 ppm and about 2500 ppm by weight of cation calculated on the total shaped porous body material. Amounts between about 50 ppm and about 2000 ppm may be most preferred.

In those embodiments of the invention wherein the alkali metal cesium is employed as a promoter in combination with other cations, the ratio of cesium to any other alkali metal and alkaline earth metal salt(s), if used, to achieve desired performance is not narrow and may vary over a wide range. The ratio of cesium to the other cation promoters may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in those catalyst embodiments comprising cesium as a promoter.

Examples of anionic promoters which may be employed in catalysts according to the present invention include halides, for example fluorides and chlorides, and oxyanions of elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications. Preferred anionic promoters suitable for use in the catalysts of this invention comprise, by way of example only, oxyanions such as sulfate, $SO_4^{-2}$, phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. Halides may also be utilized as anion promoters in the catalysts of the present invention, and include, e.g., fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

When the promoter comprises rhenium, the rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Promoters comprising manganese may also be utilized in catalysts according to the invention. The manganese species that provides the enhanced activity, efficiency and/or stability is not certain and may be the component added or that generated either during catalyst preparation or during use as a catalyst. Manganese components believed to be capable of acting as catalytic promoters, include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

Anionic promoters may be provided in any suitable promoting amount, and are typically providing in amounts ranging from about 0.0005 wt % to 2 wt %, preferably from about 0.001 wt % to 0.5 wt % based on the total weight of the catalyst. When used, the rhenium component may often be provided in amounts of at least about 1 ppm, or up to at least about 5 ppm, or even in amounts of between about 10 ppm to about 2000 ppm, or between about 20 ppm and 1000 ppm, calculated as the weight of rhenium based on the total weight of the catalyst.

The promoters for catalyst employing the present invention may also be of the type comprising at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reaction pair" refers to the pairs of atoms, molecules or ions or mixtures thereof which undergo oxidation or reduction in such half-reaction equations.

Further, the phrase "redox-half reaction pairs" is used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, and preferably are oxyanions of a polyvalent atom; that is, the atom of the anion to which oxygen is bonded is capable of existing, when bonded to a dissimilar atom, in different valence states. As used herein, the term "salt" does not indicate that the anion and cation components of the salt must be associated or bonded in the solid catalyst, but only that both components be present in some form in the catalyst under reaction conditions. Potassium is the preferred cation, although sodium, rubidium and cesium may also be utilized, and the preferred anions are nitrate, nitrite and other anions capable of forming nitrate anions under epoxidation conditions. Preferred salts include $KNO_3$ and $KNO_2$, with $KNO_3$ being most preferred.

The amount of any such salt of a member of a redox-half reaction pair utilized in catalysts according to the invention may vary widely, and generally speaking, any amount may be utilized that at least marginally enhances the efficiency of the reaction to be catalyzed. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, for example space velocity and temperature, and morphology of support. Alternatively, a suitable precursor compound may also be added such that the desired amount of the salt of a member of a redox-half reaction pair is formed in the catalyst under epoxidation conditions, especially through reaction with one or more of the gas-phase reaction components. Generally, however, a suitable range of concentration of the added efficiency-enhancing salt, or precursor thereof, calculated as cation, is about 0.01 to about 5%, preferably about 0.02 to about 3%, by weight, based on the total weight of the catalyst. Most preferably the salt is added in an amount of about 0.03 to about 2 wt. %.

The preferred gaseous efficiency-enhancing members of redox-half reaction pairs are compounds containing an element capable of existing in more than two valence states, preferably nitrogen, oxygen, or combinations of these. Most preferably, the gaseous component capable of producing a member of a redox-half reaction pair under reaction conditions is a generally a nitrogen-containing gas, such as for example nitric oxide, nitrogen dioxide and/or dinitrogen tetroxide, hydrazine, hydroxylamine or ammonia, nitroparaffins (for example, nitromethane), nitroaromatic compounds (for example nitrobenzene), N-nitro compounds, and nitriles (for example, acetonitrile).

The amount of nitrogen-containing gaseous promoter useful in catalysts according to the invention can vary widely, and is generally that amount that is sufficient to enhance the performance, e.g., the activity and/or efficiency, of the catalyst in the reaction to be catalyzed. The concentration of the nitrogen-containing gaseous promoter is determined by the particular efficiency-enhancing salt of a member of a redox-half reaction pair used and the concentration thereof, the particular alkene undergoing oxidation, and by other factors including the amount of carbon dioxide in the inlet reaction gases. For example, U.S. Pat. No. 5,504,053 discloses that when the nitrogen-containing gaseous promoter is NO (nitric oxide), a suitable concentration is from about 0.1 ppm to about 100 ppm, by volume, of the gas stream.

Although in some cases it may be preferred to employ members of the same half-reaction pair in the reaction system, that is, both the efficiency-enhancing salt promoter associated with the catalyst and the gaseous promoter in the feedstream, as, for example, with a preferred combination of potassium nitrate and nitric oxide, this is not necessary in all cases to achieve satisfactory results. Other combinations, such as $KNO_2/N_2O_3$, $KNO_3/NO_2$, $KNO_3/N_2O_4$, $KNO_2/NO$, $KNO_2/NO_2$ may also be employed in the same reaction system. In some instances, the salt and gaseous members may be found in different half-reactions which represent the first and last reactions in a series of half-reaction equations of an overall reaction.

As alluded to hereinabove, whatever the solid and/or gaseous promoter(s) employed in the present catalysts, they are desirably provided in a promoting amount. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may have enhanced activity and the same selectivity at a different set of operating conditions. Those of ordinary skill in the art may likely intentionally change the operating conditions in order to take advantage of certain catalytic properties even at the expense of other catalytic properties and will make such determinations with an eye toward maximizing profits, taking into account feedstock costs, energy costs, by-product removal costs and the like.

Whatever their amounts, it is desirable that the silver and one or more solid promoters be relatively uniformly dispersed on the shaped porous bodies. A preferred procedure for depositing silver catalytic material and one or more promoters comprises: (1) impregnating a shaped porous body according to the present invention with a solution comprising a solvent or solubilizing agent, silver complex and one or more promoters, and (2) thereafter treating the impregnated shaped porous body to convert the silver compound and effect deposition of silver and the promoter(s) onto the exterior and interior pore surfaces of the shaped porous bodies. Silver and promoter depositions are generally accomplished by heating the solution containing shaped porous bodies at elevated temperatures to evaporate the liquid within the shaped porous bodies and effect deposition of the silver and promoters onto the interior and exterior surfaces of the shaped porous bodies.

Impregnation of the shaped porous bodies is the preferred technique for silver deposition because it utilizes silver more efficiently than coating procedures, the latter being generally unable to effect substantial silver deposition onto the interior surfaces of the shaped porous bodies. In addition, coated catalysts are more susceptible to silver loss by mechanical abrasion. Whatever the manner of impregnation, the silver and one or more promoters may be impregnated simultaneously, or the promoters may be impregnated prior to, or after, the silver impregnation, and multiple impregnations may be used in order to achieve the desired weight percent of the silver and/or promoters on the shaped porous carrier.

The silver solution used to impregnate the shaped porous bodies may desirably be comprised of a silver compound in a solvent or complexing/solubilizing agent, such as any of the many silver solutions known in the art. The particular silver compound employed may be chosen, for example, from among silver complexes, silver nitrate, silver oxide, or silver carboxylates, such as silver acetate, oxalate, citrate, phthalate, lactate, propionate, butyrate and higher fatty acid salts. Silver oxide complexed with amine is a preferred form of silver for use in preparing catalysts according to the present invention.

A wide variety of solvents or complexing/solubilizing agents may be employed to solubilize silver to the desired concentration in the impregnating solution. Among those suitable for this purpose include, but are not limited to, lactic acid, ammonia, alcohols (such as ethylene glycol), amines and aqueous mixtures of amines. For example, $Ag_2O$ can be dissolved in a solution of oxalic acid and ethylenediamine to provide a concentration of approximately 30% by weight. Vacuum impregnation of such a solution onto a shaped porous body having a porosity of approximately 0.7 cc/g typically may result in a catalyst comprising approximately 25 wt % silver, based on the entire weight of the catalyst.

Accordingly, if it is desired to obtain a catalyst having a silver loading of greater than about 25 wt % or about 30 wt % or more, it would generally be necessary to subject the shaped porous bodies to at least two or more sequential impregnations of silver, with or without promoters, until the desired amount of silver is deposited on the shaped porous bodies. In some instances, the concentration of the silver salt may desirably be higher in the latter impregnation solutions than in the first. In other instances, approximately equal amounts of silver are deposited during each impregnation. Often, to effect equal deposition in each impregnation, the silver concentration in the subsequent impregnation solutions may need to be greater than that in the initial impregnation solutions. In other instances, a greater amount of silver is deposited on the shaped porous bodies in the initial impregnation than that deposited in subsequent impregnations. Each of the impregnations may be followed by roasting or other procedures to render the silver insoluble.

Well known methods can be employed to analyze the particular amounts of silver and/or solid promoters deposited onto the shaped porous bodies. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

The present invention is applicable to epoxidation reactions in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics. Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas to a catalyst-containing reactor at a temperature of from about 200° C. to about 300° C., and a pressure which may vary between about 5 atmospheres (506 kPa) and about 30 atmospheres (3.0 MPa), depending upon the mass velocity and productivity desired. Residence times in large-scale reactors are generally on the order of from about 0.1 seconds to about 5 seconds. Oxygen may be supplied to the reaction in an oxygen-containing stream, such as, air or as commercial oxygen, or as oxygen-enriched air. The resulting alkylene oxide, preferably, ethylene oxide, is separated and recovered from the reaction products using conventional methods.

The following examples are set forth for the purpose of illustrating the invention; but these examples are not intended to limit the invention in any manner. One skilled in the art will recognize a variety of substitutions and modifications of the examples that will fall within the scope of the invention.

Example 1

A. Preparation of Porous Body Precursors Having Incorporated Therein the Topography-Enhancing Additive Spodumene, and Shaped Porous Bodies Based Thereupon Porous body precursors incorporating a topography-enhancing additive are prepared in the following manner. Spodumene, $LiAl(Si_2O_6)$, is obtained from Sons of Gwalia Ltd. as spodumene concentrate. Particle size is approximately 100 to 200 US mesh. The form of the spodumene added to the other porous body precursor raw materials (transitional alumina) is the monoclinic alpha-spodumene phase or the orthorhombic beta-spodumene phase. Liquids, including water and a source of fluoride anion are added to the dry raw materials to obtain an extrudable mixture. Unless otherwise noted, the mixture is extruded in the form of cylinders or multi-partitioned cylinders with an outer diameter of about 0.38 inches, length of about 0.34 inches and wall thickness no greater than 0.075 inches or as smaller solid cylinders of about ⅛ inch diameter. After drying, the formed porous body precursors are fired to provide shaped porous bodies, i.e., so that the transitional alumina is converted to alpha-alumina. A firing temperature between 1000° C. and 1400° C. and a firing time of 45 minutes to 5 hours is used to ensure substantially complete conversion to alpha-alumina.

Figure 2:
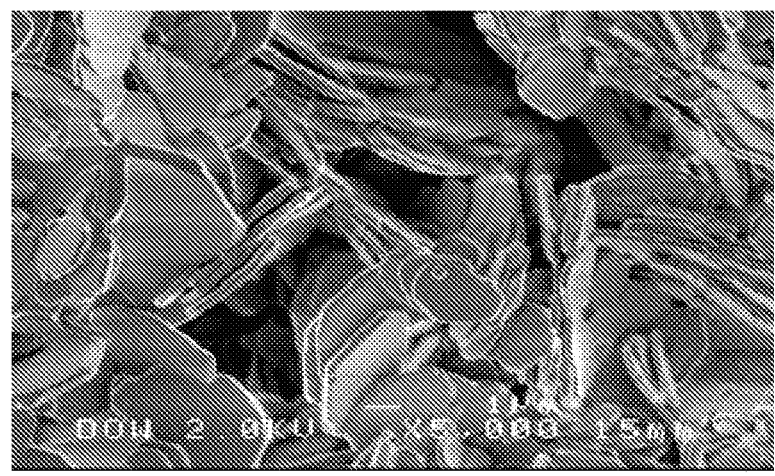
FIG. 2 depicts a scanning electron micrograph of a random sample of the inventive shaped porous body (shaped porous body ID H)/3% alpha spodumene) produced in Example 1.

FIG. 1 is a scanning electron micrograph of a random sample of comparative shaped porous body ID E, and FIG. 2 is a scanning electron micrograph of a random sample of inventive shaped porous body ID H. As can be seen, the particles of which inventive shaped porous body ID H are comprised are much thinner, and as a result, will have a greater aspect ratio than the particles of which comparative shaped porous body ID E are comprised. Additional topographical properties for the inventive shaped porous bodies so produced, including levels of spodumene in each, and comparative shaped porous bodies are given in Table I.

TABLE I

| Topographical Properties of Shaped Porous Bodies (SPBs) | | | | | | | | |
|---|---|---|---|---|---|---|---|---|
| | SPB ID | | | | | | | |
| | A | B | C | D | E | F | G | H |
| Surface Area (m²/g) | 0.87 | 0.84 | 0.93 | 1.30 | 0.81 | 0.83 | 1.05 | 1.52 |
| Total Pore Volume (cc/g) | 0.65 | 0.68 | 0.66 | 0.71 | 0.67 | 0.66 | 0.68 | 0.68 |
| Median Pore Diameter by Volume (μm) | 3.3 | 3.0 | 2.7 | 2.4 | 2.9 | 2.7 | 2.2 | 1.9 |
| Spodumene Target (Wt %) | 0 | 1 | 2 | 3 | 0 | 1 | 2 | 3 |
| Spodumene Phase | — | β | β | β | — | α | α | α |

As shown in Table I, the surface area of the inventive shaped porous bodies increases with increasing amounts of the topography-enhancing additive spodumene, while pore volume either is substantially maintained, or increases.

B. Catalyst Preparation Based Upon the Shaped Porous Bodies of 1A

Catalysts are prepared based upon the shaped porous bodies prepared according to part 1.A as follows. The shaped porous bodies are vacuum impregnated with a first impregnation silver solution typically containing 30 wt % silver oxide, 18 wt % oxalic acid, 17 wt % ethylenediamine, 6 wt % monoethanolamine, and 27 wt % distilled water. The first impregnation solution is typically prepared by (1) mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The shaped porous bodies are impregnated in an appropriately sized glass or stainless steel cylindrical vessel which is equipped with suitable stopcocks for impregnating the shaped porous bodies under vacuum. A suitable separatory funnel which is used for containing the impregnating solution is inserted through a rubber stopper into the top of the impregnating vessel. The impregnating vessel containing the shaped porous bodies is evacuated to approximately 1-2" mercury absolute for 10 to 30 minutes, after which the impregnating solution is slowly added to the shaped porous bodies by opening the stopcock between the separatory funnel and the impregnating vessel. After all the solution is emptied into the impregnating vessel (~15 seconds), the vacuum is released and the pressure returned to atmospheric. Following addition of the solution, the shaped porous bodies remain immersed in the impregnating solution at ambient conditions for 5 to 30 minutes, and are thereafter drained of excess solution for 10 to 30 minutes to provide catalysts.

The silver-impregnated catalysts are roasted as follows to effect reduction of silver on the catalyst surface. The catalysts are spread out in a single layer on stainless steel wire mesh trays, placed on a stainless steel belt (spiral weave) and transported through a 2"×2" square heating zone for 2.5 minutes, or equivalent conditions for a larger belt operation. The heating zone is maintained at 500° C. by passing hot air upward through the belt and the catalysts at the rate of 266 standard cubic feet per hour (SCFH). After being roasted in the heating zone, the catalysts are cooled in the open air to room temperature and weighed.

Next, the silver-impregnated catalysts are vacuum impregnated with a second silver impregnation solution containing both the silver oxalate amine solution and the catalyst promoters. The second impregnation solution is composed of all of the drained solution from the first impregnation plus a fresh aliquot of the first solution, or a new solution is used. The promoters, added with stirring in order to solubilize them, are added in sufficient amounts to reach the desired target levels on the finished catalysts. Promoters and stabilizers include neat cesium sulfate, cesium hydroxide solution, manganous (II) nitrate solution and diammonium EDTA solution. Two equivalents of diammonium EDTA are added with the manganese promoter in order to increase the stability of the manganese-containing ion in the impregnation solution. The impregnation, draining and roasting steps for this second impregnation are carried out analogously to the first impregnation. The finished catalysts are then employed in an ethylene epoxidation reaction, the results of which are provided hereinbelow.

The twice-impregnated finished catalysts are analyzed by XRF (results given in Table II). The promoter level targets are adjusted to shaped porous body surface area. Inventive catalysts B, C and D are compared to comparative catalyst A and inventive catalysts F, G and H are compared to comparative catalyst E. As shown, and thought to be due at least in part to the enhanced topographical properties, e.g., surface area and pore volume, of the inventive shaped porous bodies, the catalysts prepared from the inventive shaped porous bodies are, in almost every instance, able to be impregnated with greater amounts of silver and the exemplary chosen promoters.

TABLE II

Catalyst Properties

| Catalyst Properties | A comparative | B | C | D | E comparative | F | G | H |
|---|---|---|---|---|---|---|---|---|
| Added spodumene (wt %) and form | 0 | 1β | 2β | 3β | 0 | 1α | 2α | 3α |
| Ag (wt %) | 33.8 | 34.2 | 34.2 | 35.9 | 34.6 | 35.0 | 35.0 | 34.9 |
| Cs (ppm) | 460 | 481 | 534 | 780 | 553 | 514 | 618 | 912 |
| Mn (ppm) | 65 | 77 | 108 | 115 | 100 | 92 | 118 | 185 |
| SO$_4$ (ppm) | 83 | 107 | 120 | 184 | 321 | 92 | 118 | 185 |

C. Use of Inventive and Comparative Catalysts Prepared According to I.B to Catalyze Ethylene Epoxide Reactions A single-pass tubular reactor made of 0.25 inch OD stainless steel (wall thickness 0.035 inches) is used for catalyst testing. The inlet conditions of the reactor are shown in Table III.

TABLE III

Ethylene Epoxidation Process Conditions

| Component | Oxygen Process Conditions-I Mole % |
|---|---|
| Ethylene | 30.0 |
| Oxygen | 8.0 |
| Ethane | 0.5 |
| Carbon Dioxide | 6.5 |
| Nitrogen | Balance of gas |
| Parts per million Ethyl Chloride | 3.5 |
| Type of Reactor | Tube |
| Amount of Catalyst | 0.5 g |
| Total Outlet Flow Rate | 120 cc/min |

The pressure is maintained constant at about 200 psig for the tube reactors. Ethyl chloride concentration is adjusted to maintain maximum efficiency.

The catalyst test procedure is as follows: Approximately 5 g of catalyst prepared in I.B is crushed with a mortar and pestle, and then sieved to 30/50 U.S. Standard mesh. From the meshed material, 0.5 g is charged to the reactor. Glass wool is used to hold the catalyst in place. The reactor tube is fitted into a heated brass block which has a thermocouple placed against it. The block is enclosed in an insulated box. Feed gas is passed over the heated catalyst at a pressure of 200 psig. The reactor flow is adjusted and recorded at standard pressure and room temperature.

Temperature (° C.) needed to produce 1.7 mole % ethylene oxide and catalyst efficiency (selectivity) at the outlet are typically measured and regarded as indicative of catalyst performance. Measurements of activity/temperature and efficiency/selectivity are made under steady state conditions. The standard deviation of a single test result reporting catalyst efficiency in accordance with the procedures described above is about 0.5% efficiency units. The typical standard deviation of a single test result reporting catalyst activity (temperature) in accordance with the procedure described above is about 2° C. The standard deviation will depend upon the quality of the equipment and precision of the techniques used in conducting the tests, and thus will vary. The test results reported herein are believed to be within the standard deviation set forth above.

Table IV shows the temperature and selectivity of the comparative catalysts and exemplary inventive catalysts as the total cumulative production of the reactor increases over time. Inventive catalysts B, C and D are compared to comparative catalyst A and inventive catalysts F, G and H are compared to comparative catalyst E. As shown, the inventive catalysts exhibit increases in selectivity as well as improvements in activity compared to the comparative catalyst. Again, this is believed to be due at least in part to increases in surface area and pore volume provided to the base shaped porous bodies via the inclusion of the topography-enhancing additive spodumene, that in turn, allow for greater amounts of silver and promoters to be deposited thereupon, leading to the enhancements in the performance of the inventive catalysts.

Example 2

A. Preparation of Porous Body Precursors Having Incorporated Therein the Topography-Enhancing Additive Colloidal Silica, and Shaped Porous Bodies Based Thereupon Porous body precursors incorporating a topography-enhancing additive and having the shape of about ¼" O.D. and 3/32" I.D. by ¼" long rings are prepared in the following manner. An extrudable paste is prepared by mix mulling a 1:1 mixture of Versal V-250 pseudo-boehmite alumina (UOP LLC, Des Plaines, Ill. USA) and Catapal B (UOP). Colloidal silica Ludox AS-40 is added as 40% Si suspension with ammonium cation (DuPont, Del., USA). A-4M methocel (Dow Chemical Company, Midland Mich. USA), oleic acid (VWR Scientific Products, West Chester Pa. USA) and water are added and the mixture is formed using a twin-screw extruder. The formed porous body precursors are dried and calcined at between 700° C. and 1000° C.

To convert the alumina to alpha-alumina and thus provide shaped porous bodies, the formed porous body precursors are loaded into a reactor consisting of a 6 inch diameter by 22 inch long alumina tube, the reactor is evacuated, and heated to a temperature of about 840° C. After being at these conditions overnight, the reactor is filled with Freon HFC-134a to a pressure of 300 torr and held for three hours. The reactor is ramped at 2° C./min to 960° C. and held at 960° C. for 2 more hours. The reactor is cooled at 2° C./min and purged with nitrogen three times.

Topographical properties for the inventive shaped porous bodies so produced, including levels of colloidal silica in each, and comparative shaped porous bodies, are given in Table V. Surface area is measured on shaped porous bodies

TABLE IV

Figure 3:
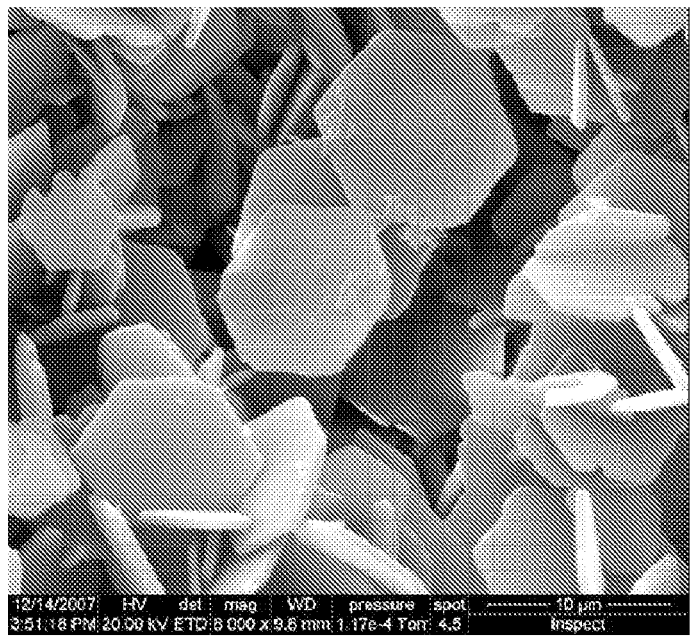
FIG. 3 depicts a scanning electron micrograph of a random sample of the comparative shaped porous body (shaped porous body ID I/comparative) produced in Example 2.
Figure 4:
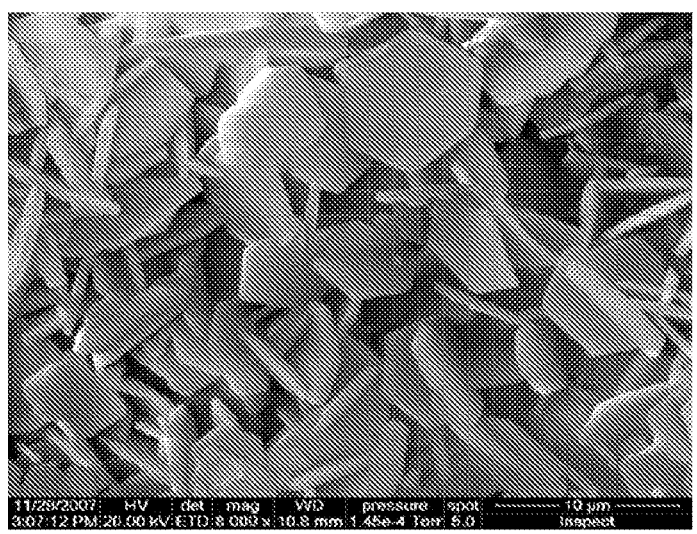
FIG. 4 depicts a scanning electron micrograph of a random sample of the inventive shaped porous body (shaped porous body ID J/0.5% colloidal Si) produced in Example 2.
Figure 5:
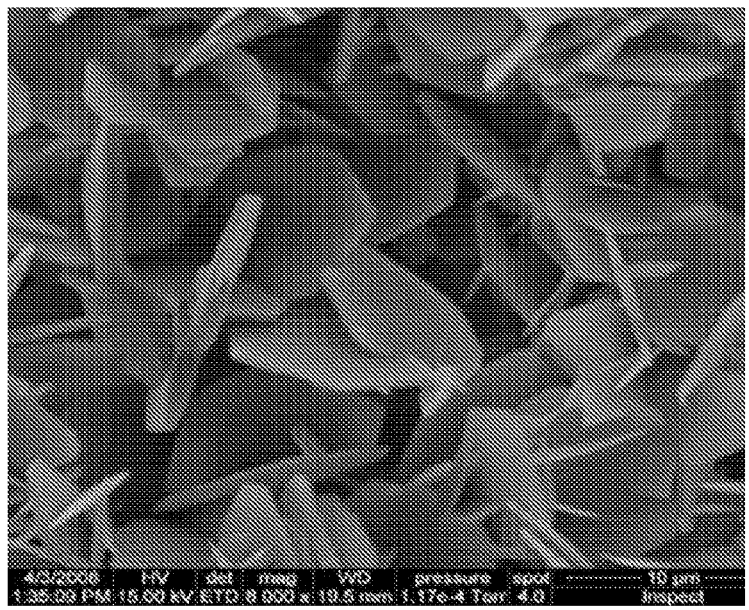
FIG. 5 depicts a scanning electron micrograph of a first random sample of the inventive shaped porous body (shaped porous body ID K/1% colloidal Si) produced in Example 2.
Figure 6:
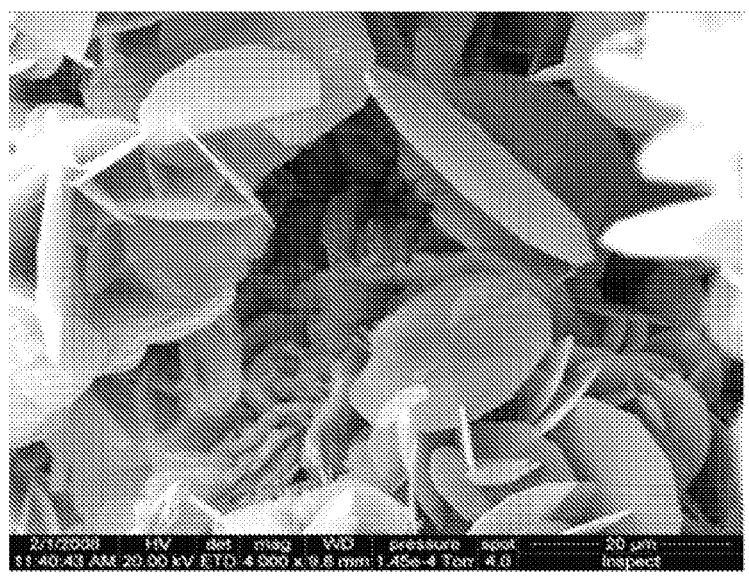
FIG. 6 depicts a scanning electron micrograph of a second random sample of the inventive shaped porous body (shaped porous body ID K/1% colloidal Si) produced in Example 2.

| | Catalyst | | | | | | | |
| --- | --- | --- | --- | --- | --- | --- | --- | --- |
| Catalyst Properties | A Comparative | B | C | D | E Comparative | F | G | H |
| Added spodumene (wt %) and form | 0 | 1β | 2β | 3β | 0 | 1α | 2α | 3α |
| Ag (wt %) | 33.8 | 34.2 | 34.2 | 35.9 | 34.6 | 35.0 | 35.0 | 34.9 |
| Cs (ppm) | 460 | 481 | 534 | 780 | 553 | 514 | 618 | 912 |
| Mn (ppm) | 65 | 77 | 108 | 115 | 100 | 92 | 118 | 185 |
| SO$_4$ (ppm) | 83 | 107 | 120 | 184 | 321 | 92 | 118 | 185 |
| Day 18 (~8M lb EO/CF) | | | | | | | | |
| Selectivity (%) | 82.9 | 82.2 | 82.9 | 82.4 | 81.9 | 82.1 | 82.1 | 82.3 |
| Temperature (C.) | 243.3 | 242.8 | 237.8 | 233.7 | 251.9 | 250.9 | 245.2 | 232.9 |
| Day 27 (~16M lb EO/CF) | | | | | | | | |
| Selectivity (%) | 82.7 | 81.7 | 82.9 | 82.6 | 81.6 | 81.7 | 81.7 | 82.5 |
| Temperature (C.) | 247.7 | 247.0 | 240.6 | 236.5 | 256.9 | 256.2 | 251.7 | 235.0 |
| Day 59 (~24M lb EO/CF) | | | | | | | | |
| Selectivity (%) | 81.8 | 81.7 | 82.4 | 82.4 | 80.5 | 80.7 | 80.9 | 82.4 |
| Temperature (C.) | 252.3 | 251.3 | 247.3 | 240.7 | 262.5 | 261.7 | 258.5 | 238.9 | after heating to 1100° C. for 2 hours. Crush strength is measured on shaped porous bodies that are not heat treated. FIG. 3 is a scanning electron micrograph (SEM) of a random sample of comparative shaped porous body ID I. FIG. 4 is a SEM of a random sample of inventive shaped porous body ID J. FIGS. 5 and 6 are SEMs of a random sample of inventive shaped porous body ID K. As shown, shaped porous bodies J and K are comprised of much thinner particles than comparative shaped porous body I. Furthermore, FIG. 6, shows the unique eight, ten or even twelve-sided surface morphology that may be provided to the particles of the shaped porous bodies via inclusion of a topography-enhancing additive in the porous body precursor.

areas provided to inventive catalysts via inclusion of the topography-enhancing additive colloidal silica, greater quantities of the silver and chosen promoters are able to be deposited on the inventive catalysts than on the comparative catalysts.

TABLE VI

| Catalyst Properties | Catalyst | | | | | |
|---|---|---|---|---|---|---|
| | L Comparative | M | N | O Comparative | P | Q |
| Added Si (wt %) | 0 | 0.5 | 1 | | 0.5 | 1 |
| Promoter 1 | $(NH_4)_2SO_4$ | $(NH_4)_2SO_4$ | $(NH_4)_2SO_4$ | $KNO_3$ | $KNO_3$ | $KNO_3$ |
| Promoter 2 | CsOH | CsOH | CsOH | $K_2Mn(EDTA)$ | $K_2Mn(EDTA)$ | $K_2Mn(EDTA)$ |
| Promoter 3 | $Mn(NO_3)_2$ | $Mn(NO_3)_2$ | $Mn(NO_3)_2$ | | | |
| Promoter 4 | $(NH_4)_2ReO_4$ | $(NH_4)_2ReO_4$ | $(NH_4)_2ReO_4$ | | | |
| Chelating Agent | $(NH_4)_2H_2(EDTA)$ | $(NH_4)_2H_2(EDTA)$ | $(NH_4)_2H_2(EDTA)$ | $(NH_4)_2H_2(EDTA)$ | $(NH_4)_2H_2(EDTA)$ | $(NH_4)_2H_2(EDTA)$ |
| Total Wt % Silver | 34 | 34 | 34 | 34 | 34 | 34 |
| Promoter 1; ppm | 151 $SO_4$ | 185 $SO_4$ | 235 $SO_4$ | 1200 K | 1650 K | 2085 K |
| Promotor 2; ppm | 585 Cs | 715 Cs | 910 Cs | 150 Mn | 150 Mn | 150 Mn |
| Promoter 3; ppm | 54 Mn | 66 Mn | 84 Mn | | | |
| Promoter 4; ppm | 270 Re | 330 Re | 420 Re | | | |

TABLE V

Topographical Properties of Shaped Porous Bodies (SPBs)

| | SPB ID | | |
|---|---|---|---|
| | I | J | K |
| Surface Area (m²/g) | 0.83 | 1.11 | 1.39 |
| Colloidal Silica Target (Wt %) | 0 | 0.5 | 1 |

As shown in Table V, shaped porous bodies incorporating the topography-enhancing additive colloidal silica have increased surface area as compared to shaped porous bodies in which no colloidal silica is incorporated (Sample ID I).

B. Catalyst Preparation Based Upon the Shaped Porous Body of 2.A

Two sets of catalysts are prepared based upon the shaped porous bodies of Example 2A in a manner analogous to that used in Example 1, except that additional promoters may be added in the second silver impregnation. The promoters, are added with stirring in order to solubilize them and are added in sufficient amounts to reach the desired target levels on the finished catalysts. Promoters and stabilizers include neat cesium sulfate, cesium hydroxide solution, manganous (II) nitrate solution, ammonium perrhenate solution, potassium manganese EDTA solution and diammonium EDTA solution. The compositions of catalysts L-Q are shown in Table VI. Inventive catalysts M and N comprise the same promoters as comparative catalyst L and are compared thereto, while inventive catalysts P and Q comprise the same promoters as comparative catalyst O and thus, are compared to catalyst Q. As is shown, and due at least in part to the enhanced surface

We claim:

1. A porous body precursor having incorporated therein at least one topography-enhancing additive selected from the group consisting of tetraethyl orthosilicate (TEOS), pure silicon, silicon ceramides, silicon containing oils or polymers, $SiF_4$, $SiCl_4$, natural or synthetic silicates, siloxanes, less than 3 wt. % colloidal silica, or combinations of these.

2. The porous body precursor of claim 1, wherein the topography-enhancing additive comprises colloidal silica.

3. A shaped porous body prepared from a porous body precursor having incorporated therein at least one topography-enhancing additive selected from the group consisting of tetraethyl orthosilicate (TEOS), pure silicon, silicon ceramides, silicon containing oils or polymers, $SiF_4$, $SiCl_4$, natural or synthetic silicates, siloxanes, less than 3 wt. % colloidal silica, or combinations of these.

4. The shaped porous body of claim 3, comprising less than 3 wt. % of the topography-enhancing additive.

5. A process for making a shaped porous body comprising incorporating into a porous body precursor at least one topography-enhancing additive selected from the group consisting of tetraethyl orthosilicate (TEOS), pure silicon, silicon ceramides, silicon containing oils or polymers, $SiF_4$, $SiCl_4$, natural or synthetic silicates, siloxanes, less than 3 wt. % colloidal silica, or combinations of these and processing the porous body precursor into a shaped porous body.

6. The process of claim 5, wherein the porous body precursor comprises one or more transition alumina precursors, transition aluminas, alpha-alumina precursors or combinations of these.

7. The process of claim 6, wherein the shaped porous body comprises transition aluminas, alpha-alumina, or combinations of these.

8. The process of claim 7, wherein at least a portion of the alpha-alumina is fluoride-affected.

9. A catalyst comprising at least one catalytic species deposited on a shaped porous body, wherein the shaped porous body is prepared from a porous body precursor having incorporated therein at least one topography-enhancing additive selected from the group consisting of tetraethyl orthosilicate (TEOS), pure silicon, silicon ceramides, silicon containing oils or polymers, $SiF_4$, $SiCl_4$, natural or synthetic silicates, siloxanes, less than 3 wt. % colloidal silica, or combinations of these.

10. A process for making a catalyst comprising:
a) selecting a shaped porous body prepared from a porous body precursor having incorporated therein at least one topography-enhancing additive selected from the group consisting of tetraethyl orthosilicate (TEOS), pure silicon, silicon ceramides, silicon containing oils or polymers, $SiF_4$, $SiCl_4$, natural or synthetic silicates, siloxanes, less than 3 wt. % colloidal silica, or combinations of these;
b) depositing at least one catalytic species on the shaped porous body.

* * * * *

UNITED STATES PATENT AND TRADEMARK OFFICE
CERTIFICATE OF CORRECTION

| | | |
|---|---|---|
| PATENT NO. | : 8,513,154 B2 | Page 1 of 1 |
| APPLICATION NO. | : 12/988316 | |
| DATED | : August 20, 2013 | |
| INVENTOR(S) | : Timothy L. Allen et al. | |

It is certified that error appears in the above-identified patent and that said Letters Patent is hereby corrected as shown below:

On the title page, item (73), Assignee, "Dow Global Technologies, LLC" should read "Dow Global Technologies LLC"

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,513,154 B2  Page 1 of 1
APPLICATION NO. : 12/988316
DATED : August 20, 2013
INVENTOR(S) : Allen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this

Fifteenth Day of September, 2015

Michelle K. Lee
*Director of the United States Patent and Trademark Office*